US00PP14127P29

(12) United States Plant Patent
Gamache et al.

(10) Patent No.: US PP14,127 P2
(45) Date of Patent: Sep. 2, 2003

(54) HOP PLANT NAMED "VGXP01"

(76) Inventors: Paul A. Gamache, 6371 Fort Rd., Toppenish, WA (US) 98948; Bernard J. Gamache, 6371 Fort Rd., Toppenish, WA (US) 98948; Steven J. Gamache, 6371 Fort Rd., Toppenish, WA (US) 98948

( * ) Notice: Subject to any disclaimer, the term of this patent is extended or adjusted under 35 U.S.C. 154(b) by 0 days.

(21) Appl. No.: 09/497,321

(22) Filed: Feb. 3, 2000

(51) Int. Cl.[7] ..... A01H 5/00
(52) U.S. Cl. ..... Plt./236
(58) Field of Search ..... Plt./236

(56) References Cited

U.S. PATENT DOCUMENTS

PP10,956 P * 6/1999 Lewis et al. ..... Plt./236

* cited by examiner

*Primary Examiner*—Bruce R. Campell
*Assistant Examiner*—Anne Marie Grünberg
(74) *Attorney, Agent, or Firm*—Stratton Ballew PLLC

(57) ABSTRACT

The new hop plant variety named 'VGXP01' is notable for its unique, pleasant aroma and relatively high alpha content. The cones of the new variety are small and compact, and grow abundantly on the mature plant.

4 Drawing Sheets

Latin name of the genus and species being claimed: *Humulus lupulus.*
Variety denomination: 'VGXP01'.

BACKGROUND AND SUMMARY OF INVENTION

This invention relates to a new and distinct variety of hop plant, and more particularly to a new hop plant variety which was asexually reproduced from a hop plant of unknown origin discovered in a cultivated hop field in Toppenish, Wash.

The new variety was first discovered in 1990 in a hop field newly planted with 'Liberty' (unpatented commercial variety) hop plants. The new variety was readily distinguishable from 'Liberty,' and so was monitored and observed during the first growing season. The large number of cones per plant and the unique aroma attracted the attention of the inventors. GLC analysis showed high alpha concentrations in the new variety, comparable to 'Galena' (unpatented commercial variety) and 'Nugget' (unpatented commercial variety) and significantly higher than 'Liberty.' Additionally, unlike 'Liberty,' the new variety was found to contain farnesene in the oil. The physical and chemical characteristics of the new variety were determined to be unlike those of any other known hop variety.

Based on the favorable analysis of the cones of the parent plant, soft wood cuttings were propagated for planting in 1991 in Toppenish, Wash. The new variety has been stably reproduced over successive generations.

BRIEF DESCRIPTION OF THE PHOTOGRAPHS

DETAILED DESCRIPTION OF THE VARIETY

Figure 1:
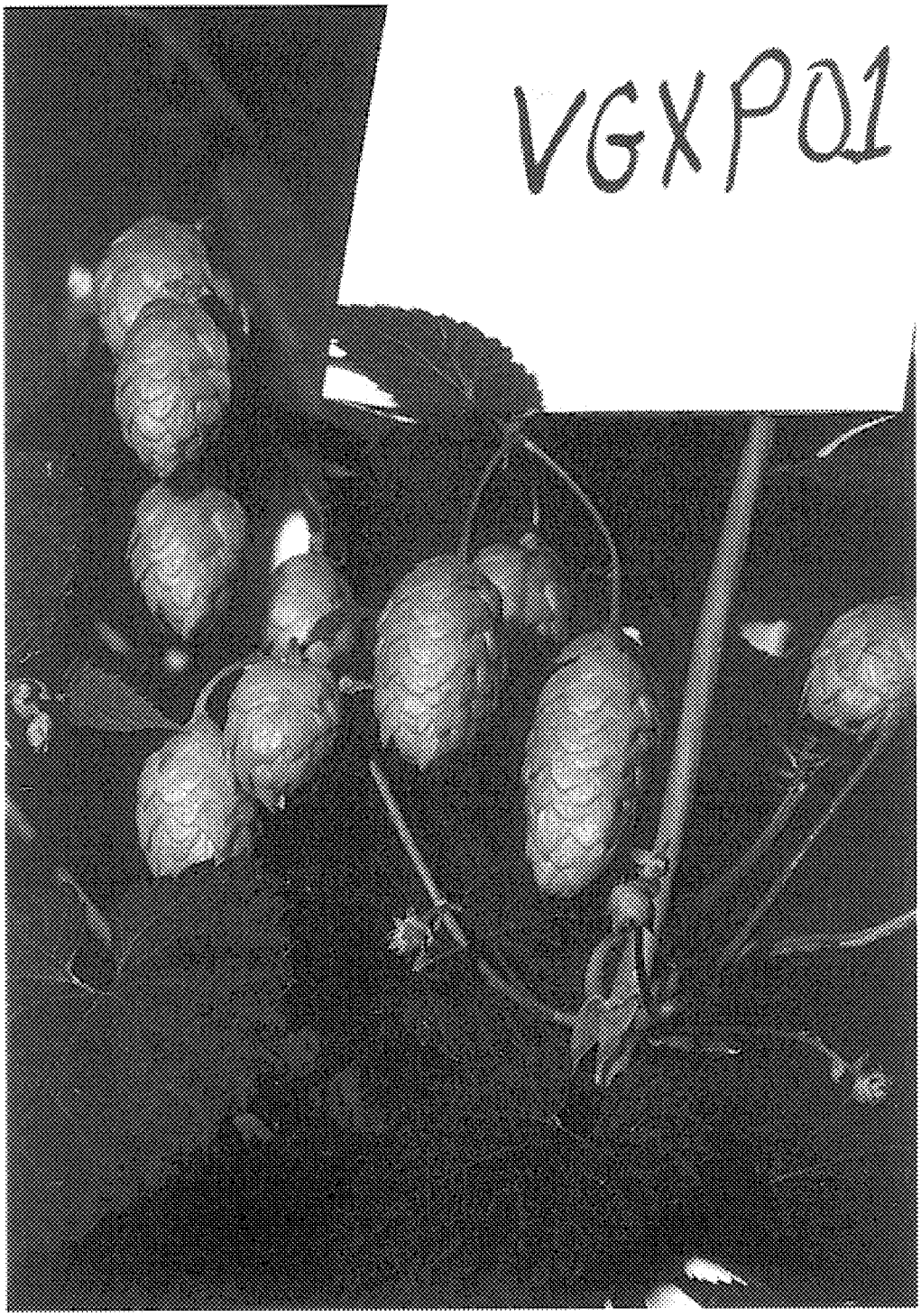
FIG. 1 depicts hop cones of the new variety.
Figure 2:
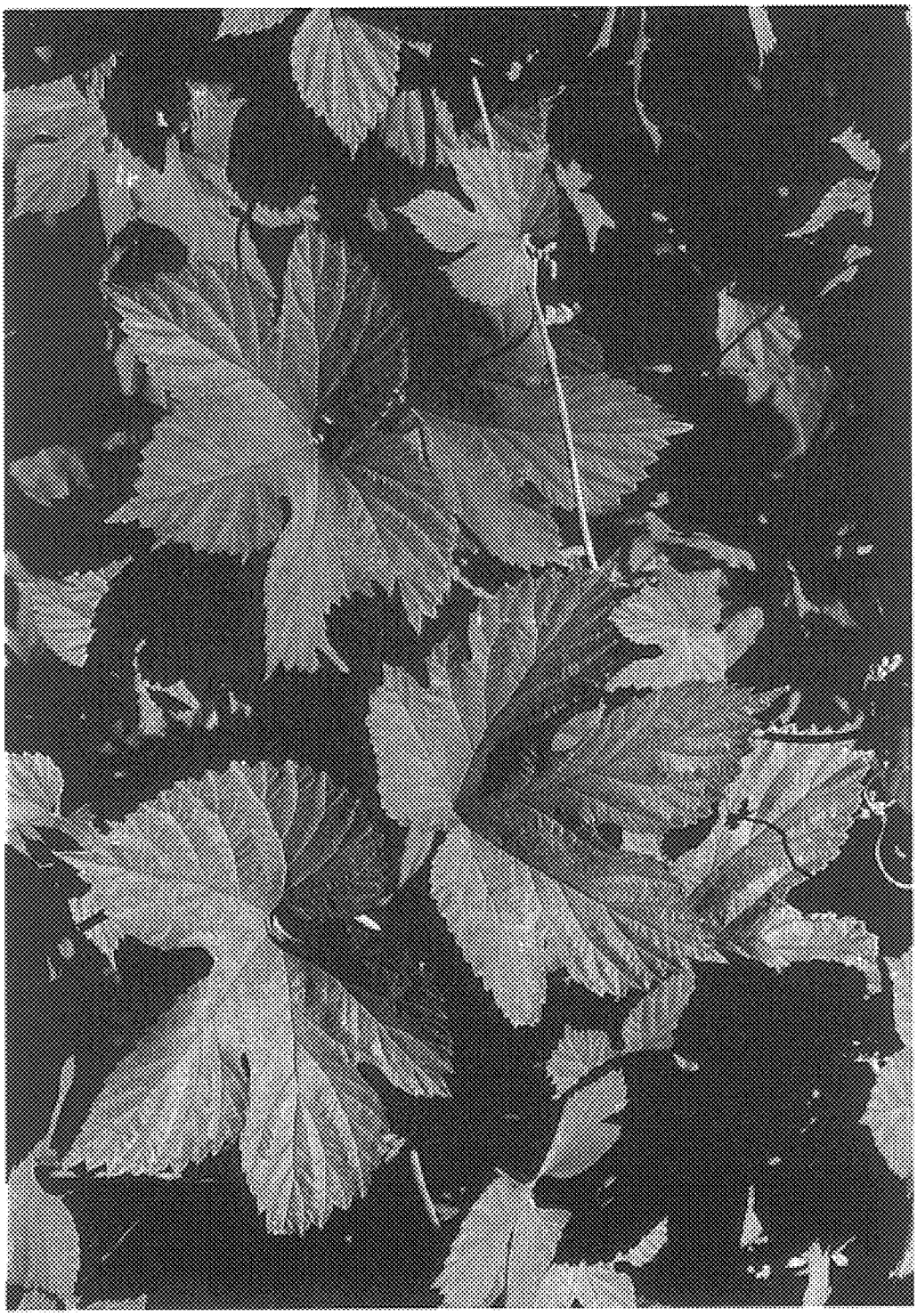
FIG. 2 depicts leaves of the new variety.
Figure 3:
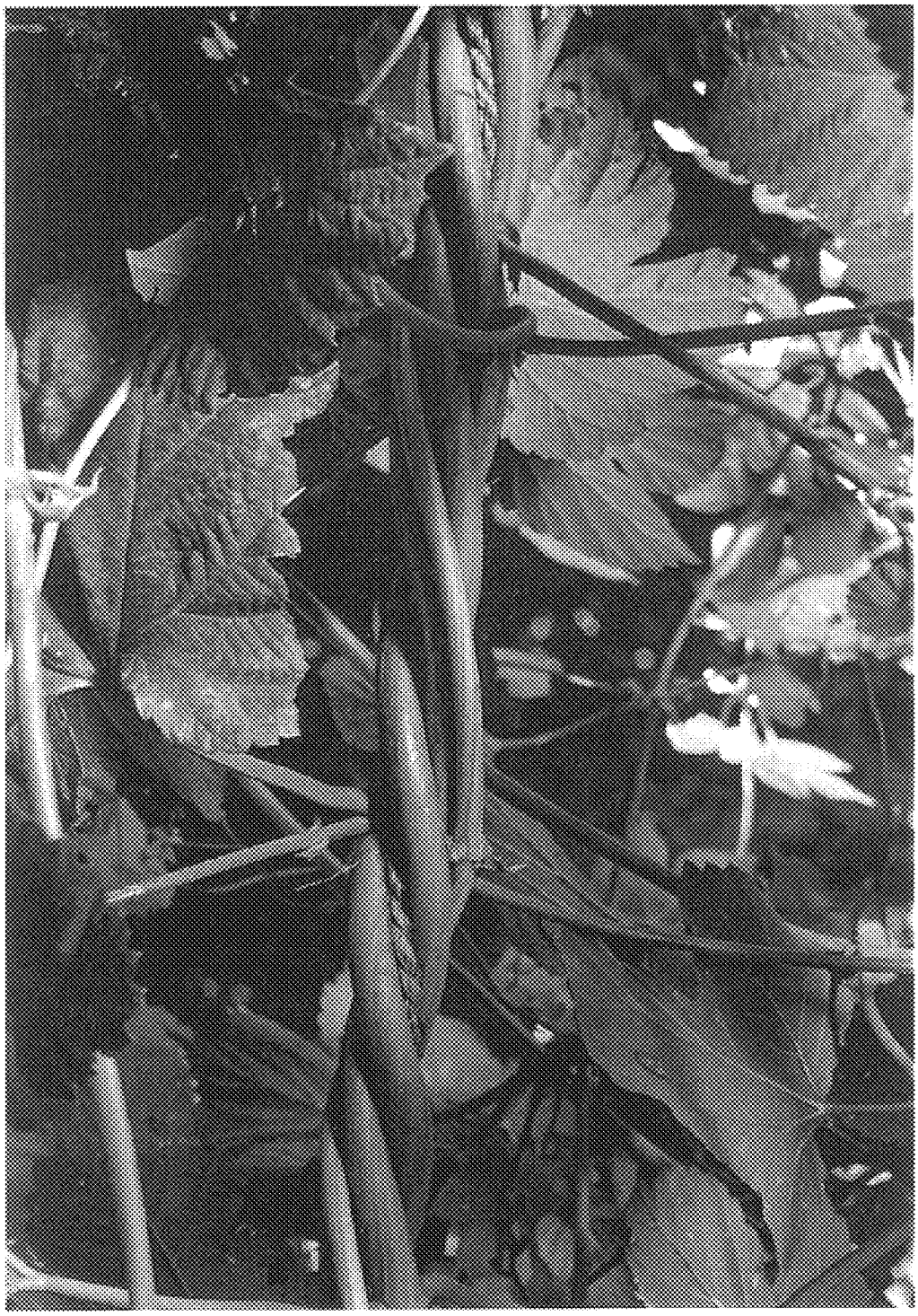
FIG. 3 depicts the bine and leaves of the new variety.
Figure 4:
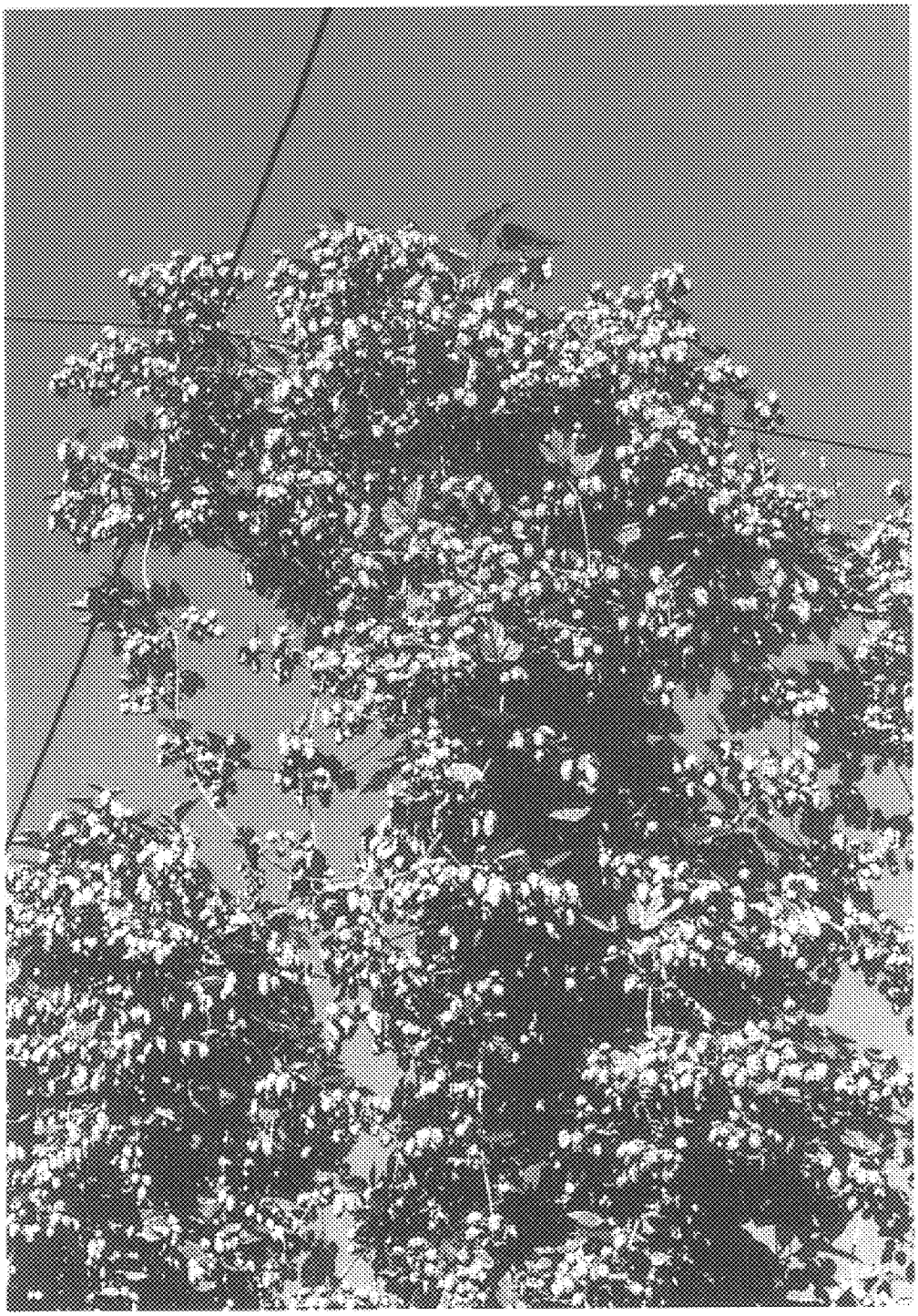
FIG. 4 depicts the upper portion of a mature hop plant of the new variety.

The new hop plant variety is notable for its unique, pleasant aroma and relatively high alpha content. The cones of the new variety are small and compact, and grow abundantly on the mature plant.

Based on a comparison of spectrophotometer readings, the new hop plant is most similar to the Yugoslavian variety 'Buket' (not patented). Both 'Buket' and 'VGXP01' have alpha levels higher than 8% and have farnesene in the oil. However, 'VGXP01' has a higher alpha level than 'Buket.'

The following is a detailed botanical description of the new and distinct variety of *Humulus lupulus,* based on observations of specimens grown in Toppenish, Wash. during the 1999, 2001, and 2002 growing seasons. All colors are described according to The Royal Horticultural Society Colour Chart. It should be understood that the botanical and analytical chemical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Bine:
- *Color.*—Yellow-green 145A.
- *Stripe.*—Present.
- *Stripe color.*—Green 138A.
- *Stipule color.*—Yellow-Green 146C.
- *Stipule direction.*—Up.
- *Average diameter.*—0.7 cm (measurement taken at 75 cm).
- *Average internode distance.*—20 cm.
- *Shoot emergence.*—After 'Cascade' (unpatented commercial variety); Before 'Galena'.

Leaves:
- *Leaf arrangement.*—Opposite.
- *Leaf shape.*—Palmate.

*Average length.*—18.8 cm.
*Average width.*—11.1 cm.
*Color — upper surface, mature.*—Green 137A.
*Color — lower surface, mature.*—Green 138B.
*Color — upper surface, immature.*—Yellow-Green 144B.
*Color — lower surface, immature.*—Yellow-Green 144C.
*Color — resin gland.*—Yellow 7A.
*Number of leaf lobes.*—3 to 5, mostly 3.
*Margin.*—Serrate.
*Average serrations per inch.*—5.5.
*Pose.*—Downward.
*Average petiole length.*—5.8 cm.
*Venation.*—Palmate.
*Vein color.*—Yellow-Green 145A.

Cones:
*Average length.*—17.6 mm.
*Average diameter.*—12.5 mm.
*Average number of cones per basal lateral node.*—91 (as many as 183 cones observed in some cases).
*Color.*—Bract tip Green 143A. Bract base Yellow green 145C. Bracteole Yellow green 145B. Lupulin glands Yellow 6A.
*Cone shape.*—Ovate.
*Cone compactness.*—Medium to tight.
*Average cone weight.*—80.6 mg.
*Bract shape.*—Ovate.
*Bract tip shape.*—Mucronate.
*Bract tip position.*—Recurved.
*Bracteole shape.*—Ovate.
*Bracteole tip shape.*—Rounded to subacute.
*Harvest maturity.*—Compare to 'Mt. Hood' (unpatented commercial variety).
*Shattering potential at harvest.*—Compare to 'Columbus' (U.S. Plant Pat. No. 10,956).
*Powdery mildew resistance.*—Moderate — Compare to 'Centennial' (unpatented commercial variety).
*Aroma.*—Sultry-sweet hop floral aroma, with highlighting citrus/orange accent notes and subtle pine undertones.

Analytical data — official spectrophotometric method:
*Alpha acids.*—8–11% (dry weight basis).
*Beta acids.*—7% (dry weight basis).
*Alpha/beta ratio.*—1.14–1.57.
*Cohumulone* (*% of alpha acids*).—24.1%.
*Total oil* (*mL oil per 100 grams*).—1.78.
*Myrcene* (*as % of total oils*).—70%.
*Caryophylene* (*as % of total oils*).—3%.
*Humulene* (*as % of total oils*).—10%.
*Farnesene* (*as % of total oils*).—3%.

We claim:

1. A new variety of hop plant, substantially as herein shown and described.

* * * * *